United States Patent
Matsui et al.

[11] Patent Number: 5,468,210
[45] Date of Patent: Nov. 21, 1995

[54] PROCESS OF THERMAL TREATMENT IN TISSUE

[75] Inventors: Masaaki Matsui; Toshifumi Shimizu; Tatsuya Kobayashi, all of Aichi, Japan

[73] Assignee: Tanaka Kikinzoku Kogyo K.K., Japan

[21] Appl. No.: 232,359

[22] Filed: Apr. 22, 1994

Related U.S. Application Data

[63] Continuation of Ser. No. 968,426, Oct. 29, 1992, abandoned.

[30] Foreign Application Priority Data

Oct. 29, 1991 [JP] Japan ................... 3-309854

[51] Int. Cl.⁶ .................................................. A61B 17/52
[52] U.S. Cl. ................................................... 600/10
[58] Field of Search ................................. 600/3–4, 7–8, 600/10–13

[56] References Cited

U.S. PATENT DOCUMENTS

| | | | |
|---|---|---|---|
| 4,574,782 | 3/1986 | Borrelli et al. | 600/10 |
| 4,697,575 | 10/1987 | Horowitz | 600/8 |
| 4,983,159 | 1/1991 | Rand | 600/12 X |
| 5,197,940 | 3/1993 | Sievert et al. | 600/13 X |
| 5,203,782 | 4/1993 | Gudov et al. | 600/12 X |

FOREIGN PATENT DOCUMENTS

| | | | |
|---|---|---|---|
| 2553244 | 5/1977 | Germany | 600/12 |

*Primary Examiner*—Angela D. Sykes
*Attorney, Agent, or Firm*—Klauber & Jackson

[57] ABSTRACT

Disclosed is a process of thermal treatment in a tissue comprising embedding an implant element in an organism and externally applying a high frequency magnetic field characterized in that the implant element comprises a magnetic exothermic member partially or completely covered with a non-magnetic insulating film.

According to the present invention, the temperature range required in the process of medical treatment in tissue (42° C. to 43° C.) can be more effectively maintained compared with a conventional magnetic exothermic member. Because of the complete coverage with an insulating film, a magnetic exothermic member having a higher Curie temperature than that of the conventional magnetic exothermic member can also be employed. The magnetic exothermic member can provide an isotropic exothermic characteristic when the powders are molded and the components of the magnetic exothermic member never dissolve in a living body.

5 Claims, 1 Drawing Sheet

PROCESS OF THERMAL TREATMENT IN TISSUE

This application is a continuation, of application Ser. No. 7/968,426, filed Oct. 29, 1992, now abandoned,

BACKGROUND OF THE INVENTION

The present invention relates to a process of thermal treatment in a tissue, and especially relates to a process of thermal treatment in a tissue comprising embedding a heat-sensitive magnetic material (hereinafter referred to as "implant") in a tumor, and externally applying a high frequency magnetic field thereto for raising the temperature of the implant in order to promote the medical treatment.

A process of thermal treatment in a tissue is one in which high frequency induction heating is utilized for medically treating a tumor in a living body in which a plurality of needle-like implant elements are embedded, based on the therapeutic effects which destroy only cancer cells to minimize the unfavorable influence on normal cells when the temperature of tissues of an organism is elevated to 42° C. to 43° C. The process of thermal treatment in a tissue is supposed to be promising not only for a brain tumor but also for other internal organ cancers such as a tongue cancer, a spleen cancer, a bladder cancer, a bone tumor, a mammary cancer and [Tatsuya Kobayashi, Yoshihisa Kida, Masaaki Matsui and Yoshifumi Amamiya, NEUROLOGICAL SURGERY, Vol. 18, No. 3 (issued on Mar. 10, 1990)]. A metallic alloy such as a Ni-Cu alloy, a Ni-Si alloy, a Ni-Pd alloy, an Fe-Pt alloy, an Fe-Pd alloy and an Fe-Pt-Si alloy and an oxide such as γ-hematite, magnetite, cementite, rare earth magnetic materials, strontium ferrite, magnet-plumbite type ferrite and amorphous materials are known as material of the implant element employed in the process of thermal treatment (Japanese patent laid open gazette No. 63-103048).

Heat generation of the above implant material of the metallic magnetic material is carried out by mainly utilizing eddy current loss, while that of the magnetic material made of an oxide or that of the powders of metallic materials are carried out by mainly utilizing magnetic hysteresis loss of powders. When the eddy current is utilized, the magnetic field is required to be applied in the longitudinal direction of a cylindrical sample for avoiding the influence of a demagnetizing field. For avoiding the directional influence of the magnetic field, the magnetic field may be rotated utilizing a Helmholz type coil which generates a magnetic field by parallel connecting the same sized coils to provide a space in the middle. Such properties as a sufficient amount of heat generation, a relatively low Curie temperature and the safety in an organism are required as implant material. It has been conventionally supposed that an Fe 73% (atomic %, any percentage appearing in the rest of the specification is also atomic %)- Pt 27% alloy having a low Curie temperature of 68° C. is most suitable.

Since, however, even the temperature of the implant element made of the Fe-Pt alloy itself rises to 68° C., there is a possibility of damaging the normal cells as well as the cancer cells by means of the heat generated. When the implant element made of the Ni-Cu alloy or the Ni-Si alloy having a similar Curie temperature to that of the Fe-Pt alloy is employed, a large number of the implant elements are required to be embedded in an affected part because of the insufficient heat generation. On the other hand, in case of the bulk-like molded material made of the powders utilizing the hysteresis loss, there are disadvantages such that when the high frequency magnetic field is applied, an eddy current flows at a contacted portion to prevent the sufficient penetration of the magnetic flux into the implant element so as to suppress the generation of heat by means of the hysteresis loss that results in the uneven heat transmission to the affected part. Although the amount of the heat generation is desirably changed according to the individual difference of a patient and the progress of the affected part, it is in fact impossible.

Further, the compatibility of the implant element to an organism including the dispersion of the component elements into the organism as a result of corrosion and ionization is problematic even if such a metal as Fe and Pt is a metal of considerably low toxicity because the implant element is embedded in the organism for a long period of time. The molded member made of powders such as ceramics becomes brittle after the repetition of the thermal treatments in a tissue so that the uncovered powders are in danger of straying in the living body.

SUMMARY OF THE INVENTION

The present invention has been made to overcome the above disadvantages.

An object of the present invention is to provide a process of thermal treatment in tissue employing a magnetic exothermic member which can maintain the temperature of the tissue in the desirable temperature range between 42° to 43° C. required in the process of thermal treatment in tissue.

Another object of the invention is to provide a process of thermal treatment in tissue which can be conducted without the dissolution of a hazardous metal into a living body.

A further object of the invention is to provide a process of thermal treatment in tissue which can be conducted without the deterioration of the magnetic exothermic member covered with an non-magnetic insulating film which is liable to occur due to the repetition of the temperature rise.

This invention is a process of thermal treatment in a tissue comprising embedding an implant element in an organism and externally applying a high frequency magnetic field characterized in that the implant element comprises a magnetic exothermic member partially or completely covered with a non-magnetic insulating film.

BRIEF DESCRIPTION OF THE DRAWING

In FIG. 1, ① and ② diagrams showing the relation in an agar phantom, ③ is a diagram showing the relation in a normal muscle tissue of a rabbit and ④ is a diagram showing the relation in a cancer tissue of a rabbit.

DETAILED DESCRIPTION OF THE INVENTION

Figure 1:
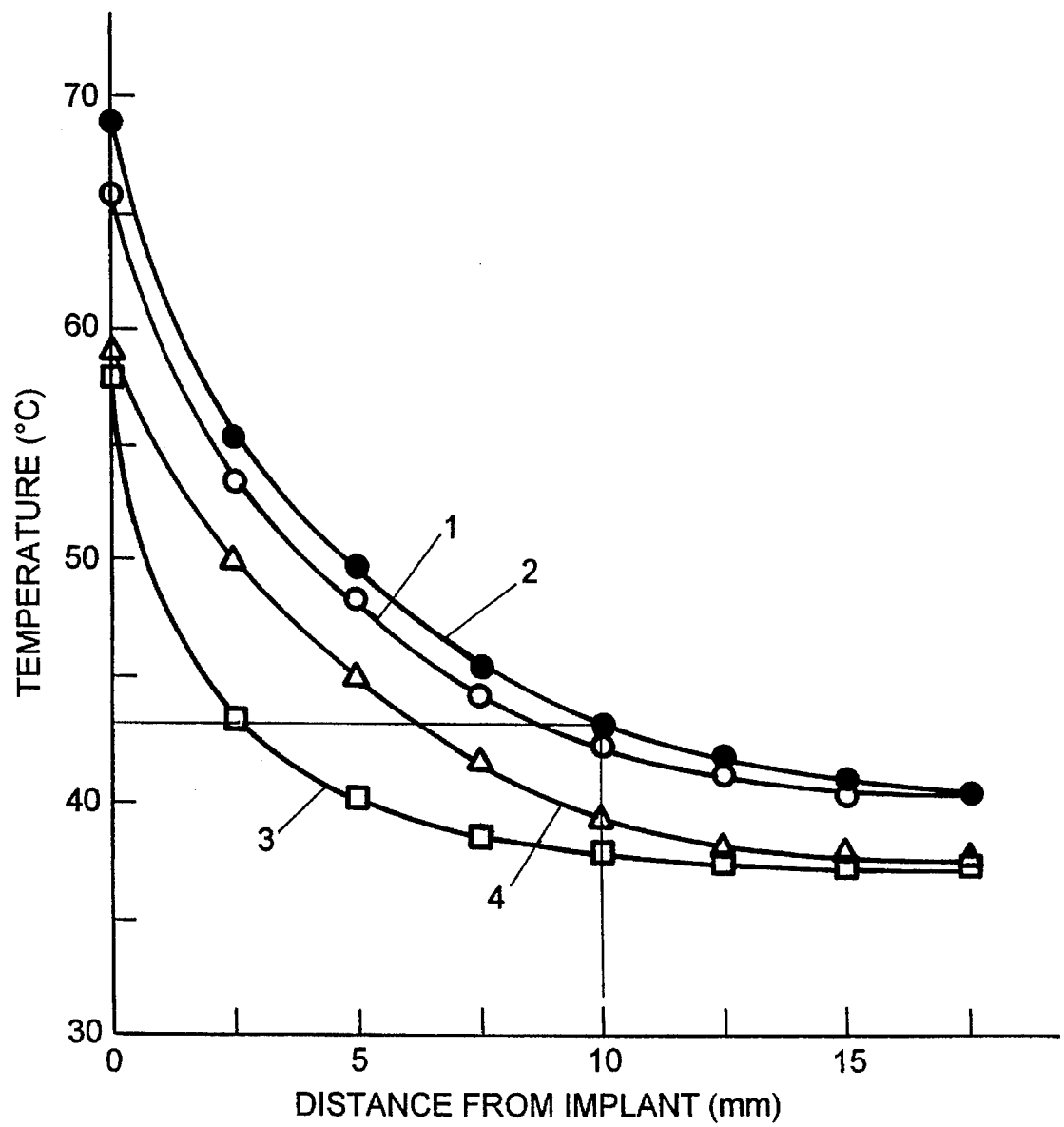
FIG. 1 is a graph showing a relation of a temperature change to a distance from an implant applied with a high frequency magnetic field.

The invention can be carried out in a variety of aspects such that the implant element is made needle-like, the magnetic exothermic member is made of a metal or an alloy, or powders of ceramics and the non-magnetic insulating element is a silicon compound.

In the present invention, the non-magnetic insulating film is equipped for controlling the amount of heat generated on the magnetic exothermic member which may be too large for maintaining the temperature of a tissue in an appropriate temperature range of 42° C. to 43° C.

The thickness of the non-magnetic insulating film depends on the Curie temperature of the magnetic exothermic member employed. The thickness is so adjusted that it is made thinner when such a low Curie temperature alloy as an Ni-Si(4% in weight) alloy (60° C.) and an Fe-Pt alloy (68° C.) is employed and it is made thicker in case of such high Curie temperature material as Fe-Ca-Mg-O ceramics (Curie temperature: 94° C.), Fe-Ca-Si-N ceramics and an Fe-Pd (30%) alloy (Curie temperature: 230° C.). It have been found that the temperature range of 42° C. to 43° C. can be maintained by equipping the non-magnetic insulating film on the magnetic exothermic member. This enables the implant element to be located at a pertinent position.

As mentioned, according to the present invention, the temperature range required in the process of medical treatment in tissue (42° C. to 43° C.) can be more effectively maintained compared with a conventional magnetic exothermic member. Because of the partial or complete coverage with an insulating film, a magnetic exothermic member having a higher Curie temperature than that of the conventional magnetic exothermic member can also be employed. The magnetic exothermic member can provide an isotropic exothermic characteristic when the powders are molded and the components of the magnetic exothermic member never dissolve in a living body.

EXAMPLES

Examples of the present invention will be described together with Comparative Examples for further clarifying the characteristics of the present invention.

EXAMPLE 1

It was adjusted that a high frequency magnetic field of 1650 A/m was generated in the center of an induction coil having a diameter of 30 cm employing an apparatus for generating a high frequency magnetic field of which an output was 2.5 kW and of which a frequency was 240 kHz. An implant element was prepared by dipping a rod made of an Fe-Pt (27.4%) alloy (diameter: 1.8 mm, length: 20 mm, Curie temperature: 68° C.) in a phosphoric acid aqueous solution containing 3-aminopropyl triethoxysilane ($NH_2(CH)_2Si(OC_2H_5)_3$) followed by thermal decomposition to produce a coating of $SiO_2$ film having a thickness of 10 μm and was employed. The measurement of the temperature to the distance of the implant element was performed in an agar phantom [① of FIG. 1].

COMPARATIVE EXAMPLE 1

The implant element was prepared according to the same conditions as those of Example 1 except that the glass coating was not formed. The measurement results were shown as ②, ③ and ④ of FIG. 1. The measurement of ② of FIG. 1 was performed in the agar phantom, ③ of FIG. 1 was in a normal muscle tissue of a rabbit, and ④ of FIG. 1 was in a cancer tissue (VX7) of a rabbit.

It is found comparing the lines of ① and ② that in case of the implant element of Example 1 (①), the temperature range of 42° C. to 43° C. lower than that of the implant element of Comparative Example 1 (②) by 5° C. could be properly controlled. In other words, the implant element according to the individual difference and the progress of the affected part can be supplied by changing the thickness of the coating.

COMPARATIVE EXAMPLE 2

The sintered powders of an Fe(72.6%)-Pt(27.4%) alloy (Curie temperature: 63° C.) having a grain size of 230 to 350 mesh were embedded in the muscle around a femur of a white rabbit. The tissues around the alloy was analyzed by means of X-ray detecting a slight amount of Fe. This sample was subjected to a dipping test in a physiological salt solution containing 0.9% of NaCl and of which pH was 5.5 (adjusted by means of a phosphoric acid) to result in the decrease of 10 mg/cm². month.

EXAMPLE 2

The powers of Comparative Example 2 were dipped in the Si-phosphoric acid aqueous solution to obtain Fe-Pt alloy powders coated with an $SiO_2$ glass film having a thickness of 1 to 2 μm. No dissolution occurred when 1 g of the powders were added into a physiological saline.

What is claimed is:

1. A process of thermal treatment in a tissue comprising embedding a needle-like implant element in an organism and externally applying a high frequency magnetic field so as to generate heat utilizing eddy current loss characterized in that the implant element comprises a magnetic exothermic electroconductive member at least part of which is covered with a non-magnetic film having thermally insulating properties; wherein the film controls the amount of heat generated from the magnetic exothermic electroconductive member reaching said tissue with the application of the high frequency magnetic field, and said film thereby preventing excessive generated heat, detrimental to said tissue, from reaching said tissue.

2. The process of medical treatment in a tissue as claimed in claim 1, wherein the magnetic exothermic electroconductive member is completely covered with the non-magnetic thermally insulating film.

3. The process of medical treatment in a tissue as claimed in claim 1, wherein the magnetic exothermic electroconductive member is made of a member of the group consisting of metal, a metal alloy; and an amorphous material.

4. The process of medical treatment in a tissue as claimed in claim 1, wherein the non-magnetic thermally insulating film is a silicon compound.

5. The process of claim 1, wherein the element results in the controlled generation of heat to reach the tissue in an amount sufficient to maintain a temperature in the range between 42° C. to 43° C.

\* \* \* \* \*